United States Patent
Kwok et al.

(10) Patent No.: US 7,207,335 B2
(45) Date of Patent: Apr. 24, 2007

(54) MASK AND VENT ASSEMBLY THEREFOR

(75) Inventors: Philip Rodney Kwok, Chatswood (AU); Perry David Lithgow, Glenwood (AU)

(73) Assignee: ResMed Limited, Bella Vista (AU)

( * ) Notice: Subject to any disclaimer, the term of this patent is extended or adjusted under 35 U.S.C. 154(b) by 23 days.

(21) Appl. No.: 10/364,358

(22) Filed: Feb. 12, 2003

(65) Prior Publication Data

US 2003/0116160 A1 Jun. 26, 2003

Related U.S. Application Data

(63) Continuation of application No. 09/021,541, filed on Feb. 10, 1998, now Pat. No. 6,561,190.

(30) Foreign Application Priority Data

Feb. 10, 1997 (AU) .................................... PO5045

(51) Int. Cl.
*A62B 18/10* (2006.01)
(52) U.S. Cl. ..................... 128/207.12; 128/207.16; 128/205.24; 128/206.12; 128/206.21
(58) Field of Classification Search ........... 128/207.12, 128/207.16, 205.24, 204.18, 206.12, 206.21
See application file for complete search history.

(56) References Cited

U.S. PATENT DOCUMENTS

| 781,516 | A | 1/1905 | Guthrie |
| 812,706 | A | 2/1906 | Warbasse |
| 835,075 | A | 11/1906 | Mahaffy |
| 1,081,745 | A | 2/1913 | Johnston et al. |
| 1,192,186 | A | 7/1916 | Greene |
| 1,653,572 | A | 12/1927 | Jackson |
| 1,926,027 | A | 9/1933 | Biggs |
| 2,008,677 | A | * 7/1935 | Booharin ............... 128/206.15 |
| 2,102,037 | A | * 12/1937 | Schwartz ............... 128/206.15 |
| 2,123,353 | A | 7/1938 | Catt |
| 2,248,477 | A | 7/1941 | Lombard |
| 2,254,854 | A | 9/1941 | O'Connell |
| 2,317,608 | A | 4/1943 | Heidbrink |
| 2,371,965 | A | 3/1945 | Lehmberg |
| 2,376,871 | A | 5/1945 | Fink |
| 2,415,846 | A | 2/1947 | Randall |
| 2,438,058 | A | 3/1948 | Kincheloe |
| 2,578,621 | A | 12/1951 | Yant |
| 2,872,923 | A | 2/1959 | Birch et al. |
| 2,931,356 | A | 4/1960 | Schwarz |
| D188,084 | S | 5/1960 | Garelick |

(Continued)

FOREIGN PATENT DOCUMENTS

AU 91/77110 B 11/1991

(Continued)

OTHER PUBLICATIONS

Mask 1 Photographs, Respironics Inc., Reusable Full Mask (small) Part # 452033 Lot #951108.

(Continued)

*Primary Examiner*—Anhtuan T. Nguyen
*Assistant Examiner*—Darwin P Erezo
(74) *Attorney, Agent, or Firm*—Nixon & Vanderhye P.C.

(57) ABSTRACT

A mask (10) for use with a system for supplying breathable gas pressurised above atmospheric pressure to a human or animal's airways. The mask (10) includes a mask shell (12) which is, in use, in fluid communication with a gas supply conduit (30), and a gas washout vent assembly (20). At least the region of the mask shell (12) or conduit (30) surrounding or adjacent the vent assembly is formed from a relatively flexible elastomeric material.

53 Claims, 6 Drawing Sheets

U.S. PATENT DOCUMENTS

| | | | |
|---|---|---|---|
| 2,939,458 A | 6/1960 | Lundquist | |
| 3,013,556 A | 12/1961 | Galleher | |
| 3,162,411 A * | 12/1964 | Duggan | 248/56 |
| 3,189,027 A | 6/1965 | Bartlett | |
| 3,238,943 A | 3/1966 | Holley | |
| 3,315,674 A | 4/1967 | Bloom et al. | |
| 3,330,273 A | 7/1967 | Bennett | |
| 3,362,420 A | 1/1968 | Blackburn et al. | |
| 3,363,833 A | 1/1968 | Laerdal | |
| 3,412,231 A * | 11/1968 | McElligott | 219/201 |
| 3,556,122 A | 1/1971 | Laerdal | |
| 3,580,051 A | 5/1971 | Blevins | |
| 3,680,556 A | 8/1972 | Morgan | |
| 3,700,000 A | 10/1972 | Hesse et al. | |
| 3,720,235 A | 3/1973 | Schrock | |
| 3,796,216 A | 3/1974 | Schwarz | |
| 3,799,164 A | 3/1974 | Rollins | |
| D231,803 S | 6/1974 | Huddy | |
| 3,868,164 A | 2/1975 | Lisk | |
| 3,877,425 A | 4/1975 | O'Neill | |
| 3,942,403 A | 3/1976 | Pramberger | |
| 3,958,275 A | 5/1976 | Morgan et al. | |
| 4,037,142 A * | 7/1977 | Poole | 361/520 |
| 4,077,404 A | 3/1978 | Elam | |
| D250,131 S | 10/1978 | Lewis et al. | |
| 4,167,185 A | 9/1979 | Lewis | |
| 4,219,020 A | 8/1980 | Czajka | |
| 4,226,234 A | 10/1980 | Gunderson | |
| 4,245,632 A | 1/1981 | Houston | |
| 4,274,406 A | 6/1981 | Bartholomew | |
| 4,276,877 A | 7/1981 | Gdulla | |
| D262,322 S | 12/1981 | Mizerak | |
| 4,304,229 A | 12/1981 | Curtin | |
| 4,328,797 A | 5/1982 | Rollins, III et al. | |
| 4,347,205 A | 8/1982 | Stewart | |
| 4,354,488 A | 10/1982 | Bartos | |
| 4,402,316 A | 9/1983 | Gadberry | |
| 4,412,537 A | 11/1983 | Tiger | |
| 4,440,163 A | 4/1984 | Spergel | |
| 4,454,881 A | 6/1984 | Huber et al. | |
| 4,467,799 A | 8/1984 | Steinberg | |
| 4,522,639 A | 6/1985 | Ansite et al. | |
| 4,558,710 A | 12/1985 | Eichler | |
| 4,559,939 A | 12/1985 | Levine et al. | |
| 4,580,556 A * | 4/1986 | Kondur | 128/206.28 |
| 4,616,647 A | 10/1986 | McCreadie | |
| 4,622,964 A | 11/1986 | Flynn | |
| 4,648,394 A | 3/1987 | Wise | |
| 4,649,912 A | 3/1987 | Collins | |
| 4,655,213 A | 4/1987 | Rapoport et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A | 7/1987 | Wilcox | |
| D293,613 S | 1/1988 | Wingler | |
| 4,739,755 A | 4/1988 | White et al. | |
| 4,770,169 A | 9/1988 | Schmoegner et al. | |
| 4,774,941 A | 10/1988 | Cook | |
| 4,782,832 A | 11/1988 | Trimble et al. | |
| 4,799,477 A | 1/1989 | Lewis | |
| 4,809,692 A | 3/1989 | Nowacki et al. | |
| 4,819,629 A | 4/1989 | Jonson | |
| 4,821,713 A | 4/1989 | Bauman | |
| 4,841,953 A | 6/1989 | Dodrill | |
| 4,848,334 A | 7/1989 | Bellm | |
| 4,848,366 A | 7/1989 | Aita et al. | |
| 4,907,584 A | 3/1990 | McGinnis | |
| 4,910,806 A | 3/1990 | Baker et al. | |
| 4,919,128 A | 4/1990 | Kopala et al. | |
| 4,938,210 A | 7/1990 | Shene | |
| 4,938,212 A | 7/1990 | Gnook et al. | |
| 4,944,310 A | 7/1990 | Sullivan | |
| D310,431 S | 9/1990 | Bellm | |
| 4,971,051 A | 11/1990 | Toffolon | |
| 4,974,586 A * | 12/1990 | Wandel et al. | 128/206.28 |
| 4,986,269 A | 1/1991 | Hakkinen | |
| 4,989,596 A | 2/1991 | Macris et al. | |
| 4,989,599 A | 2/1991 | Carter | |
| 5,005,568 A | 4/1991 | Loescher et al. | |
| 5,005,571 A | 4/1991 | Dietz | |
| 5,018,519 A | 5/1991 | Brown | |
| 5,038,776 A | 8/1991 | Harrison et al. | |
| 5,042,473 A | 8/1991 | Lewis | |
| 5,042,478 A | 8/1991 | Kopala et al. | |
| 5,046,200 A | 9/1991 | Feder | |
| 5,046,512 A | 9/1991 | Murchie | |
| 5,063,922 A | 11/1991 | Hakkinen | |
| 5,065,756 A | 11/1991 | Rapoport | |
| 5,069,205 A | 12/1991 | Urso | |
| 5,080,094 A | 1/1992 | Tayebi | |
| D323,908 S | 2/1992 | Hollister et al. | |
| 5,109,839 A | 5/1992 | Blasdell et al. | |
| 5,109,840 A | 5/1992 | Daleiden | |
| 5,121,745 A | 6/1992 | Israel | |
| 5,133,347 A | 7/1992 | Huennebeck | |
| 5,140,982 A | 8/1992 | Bauman | |
| 5,159,938 A | 11/1992 | Laughlin | |
| 5,178,138 A | 1/1993 | Walstrom et al. | |
| D334,633 S | 4/1993 | Rudolph | |
| 5,231,983 A | 8/1993 | Matson et al. | |
| 5,233,978 A | 8/1993 | Callaway | |
| 5,243,971 A | 9/1993 | Sullivan | |
| 5,265,595 A | 11/1993 | Rudolph | |
| 5,279,289 A | 1/1994 | Kirk | |
| 5,280,784 A | 1/1994 | Kohler | |
| 5,297,544 A | 3/1994 | May | |
| 5,311,862 A | 5/1994 | Blasdell et al. | |
| 5,322,057 A | 6/1994 | Raabe et al. | |
| 5,343,878 A | 9/1994 | Scarberry et al. | |
| 5,357,951 A | 10/1994 | Ratner | |
| 5,368,020 A | 11/1994 | Beux | |
| 5,372,130 A | 12/1994 | Stern et al. | |
| 5,388,571 A | 2/1995 | Roberts et al. | |
| 5,404,871 A | 4/1995 | Goodman et al. | |
| 5,419,318 A | 5/1995 | Tayebi | |
| 5,429,126 A | 7/1995 | Bracken | |
| 5,429,683 A | 7/1995 | Le Mitouard | |
| 5,431,158 A | 7/1995 | Tirotta | |
| 5,438,981 A | 8/1995 | Starr et al. | |
| 5,441,046 A | 8/1995 | Starr et al. | |
| D362,061 S | 9/1995 | McGinnis et al. | |
| 5,477,852 A | 12/1995 | Landis | |
| 5,479,920 A | 1/1996 | Piper et al. | |
| 5,488,948 A | 2/1996 | Dubruille et al. | |
| 5,492,116 A | 2/1996 | Scarberry et al. | |
| 5,501,214 A | 3/1996 | Sabo | |
| 5,509,404 A | 4/1996 | Lloyd et al. | |
| 5,517,986 A | 5/1996 | Starr et al. | |
| 5,538,000 A | 7/1996 | Rudolph | |
| 5,540,223 A | 7/1996 | Starr et al. | |
| 5,542,128 A | 8/1996 | Lomas | |
| RE35,339 E | 10/1996 | Rapoport | |
| 5,560,354 A | 10/1996 | Berthon-Jones et al. | |
| 5,570,682 A | 11/1996 | Johnson | |
| 5,570,689 A | 11/1996 | Starr et al. | |
| 5,575,277 A * | 11/1996 | Lutz et al. | 128/201.18 |
| D377,089 S | 12/1996 | Starr et al. | |
| 5,592,938 A | 1/1997 | Scarberry et al. | |
| 5,608,647 A | 3/1997 | Rubsamen et al. | |
| 5,642,730 A | 7/1997 | Baran | |
| 5,645,049 A | 7/1997 | Foley et al. | |
| 5,647,355 A | 7/1997 | Starr et al. | |
| 5,647,357 A | 7/1997 | Barnett et al. | |
| 5,649,532 A | 7/1997 | Griffiths | |

| | | | |
|---|---|---|---|
| 5,649,533 A | 7/1997 | Oren | |
| 5,655,520 A | 8/1997 | Howe et al. | |
| 5,655,527 A | 8/1997 | Scarberry et al. | |
| 5,657,493 A | 8/1997 | Ferrero et al. | |
| 5,657,752 A | 8/1997 | Landis et al. | |
| 5,662,101 A | 9/1997 | Ogden et al. | |
| 5,666,946 A | 9/1997 | Langenback | |
| 5,685,296 A | 11/1997 | Zdrojkowski et al. | |
| 5,687,715 A | 11/1997 | Landis et al. | |
| 5,715,814 A | 2/1998 | Ebers | |
| 5,732,695 A | 3/1998 | Metzger | |
| 5,746,201 A | 5/1998 | Kidd | |
| 5,765,553 A | 6/1998 | Richards et al. | |
| 5,813,423 A | 9/1998 | Kirchgeorg | |
| 5,832,918 A | 11/1998 | Pantino | |
| 5,921,239 A | 7/1999 | McCall et al. | |
| 6,006,748 A | 12/1999 | Hollis | |
| 6,019,101 A | 2/2000 | Cotner et al. | |
| 6,039,044 A * | 3/2000 | Sullivan | 128/205.25 |
| 6,135,109 A | 10/2000 | Blasdell et al. | |
| 6,561,190 B1 * | 5/2003 | Kwok | 128/207.12 |
| 6,561,191 B1 * | 5/2003 | Kwok | 128/207.12 |
| 6,668,830 B1 * | 12/2003 | Hansen et al. | 128/206.21 |

FOREIGN PATENT DOCUMENTS

| | | |
|---|---|---|
| AU | 94/64816 B | 12/1994 |
| AU | 95/16178 B | 7/1995 |
| AU | 9459430 | 2/1996 |
| AU | A 32914/95 | 2/1996 |
| AU | A 41018/97 | 4/1998 |
| AU | A 89312/98 | 1/1999 |
| CA | 1039144 | 9/1978 |
| DE | 459104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 A1 | 4/1987 |
| DE | 3539073 A1 | 5/1987 |
| DE | 4004157 C1 | 4/1991 |
| DE | 4343205 A1 | 6/1995 |
| DE | 197 35 359 | 1/1998 |
| DE | 297 23 101 | 7/1998 |
| DE | 298 10846 U1 | 8/1998 |
| EP | 0 054 154 | 10/1981 |
| EP | 0 252 052 A1 | 1/1988 |
| EP | 0 264 772 A1 | 4/1988 |
| EP | 0 386 605 A1 | 2/1990 |
| EP | 0427474 A2 | 5/1991 |
| EP | 0 462 701 A1 | 12/1991 |
| EP | 0 602 424 | 11/1993 |
| EP | 0601708 | 6/1994 |
| EP | 0 608 684 A1 | 8/1994 |
| EP | 0 697 225 | 7/1995 |
| EP | 0697 225 A2 | 7/1995 |
| EP | 178 925 A2 | 4/1996 |
| EP | 0 747 078 A2 | 12/1996 |
| EP | 0 821 978 | 2/1998 |
| FR | 2 574 657 A1 | 6/1986 |
| FR | 2 658 725 A1 | 8/1991 |
| FR | 2 749 176 | 12/1997 |
| GB | 1395391 | 5/1975 |
| GB | 1 467 828 | 3/1977 |
| GB | 2145335 A | 3/1985 |
| GB | 2147506 A | 5/1985 |
| GB | 2 164 569 A | 3/1986 |
| GB | 2 236 681 A | 4/1991 |
| GB | 2 267 648 A | 12/1993 |
| JP | 63105772 | 5/1988 |
| JP | 7000521 | 1/1995 |
| JP | 9010311 | 1/1997 |
| JP | 09/216240 A | 8/1997 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/48878 | 11/1998 |

OTHER PUBLICATIONS

Mask 2 Photographs, Puritan—Bennett, Adam Curcuit , Shell Part # 231700, Swivel Part # 616329-00, Pill ws (medium) Part #616324.

Mask 3, Photographs, DeVilbiss Healthcare Inc., DeVilbiss Seal-Ring and CPAP Mask Kit (medium), Part 73510-669.

Mask 4 Photographs, Respironics Inc., Monarch Mini Mask with Pressure Port. Part # 572004, Monarch Headgear, Part # 572011.

Mask 5 Photographs, Healthdyne Technologies, Nasal CPAP Mask (medium narrow), Part # 702510.

Mask 6 Photographs, Healthdyne Technologies, Soft Series Nasal CPAP Mask, Part # 702020.

Mask 7 Photographs, DeVilbiss Healthcare Inc., Small Mask and Seal Rings, Part # 73510-668.

Mask 8 Photographs, Respironics Inc., Reusable Contour Mask (medium), Part # 302180.

Mask 9 Photographs, Healthdyne Technologies, Healthdyne Large Headgear.

Mask 10 Photographs, Respironics Inc., Soft Cap (medium), Part # 302142.

Mask 11 Photographs, Weinmann: Hamburg, Nasalmaskensystem mit Schalldämpfer (medium), Part # WN 23105.

Mask 12 Photographs, Life Care.

Mask 13 Photographs, Healthdyne Technologies.

Mask 14 Photograph, King System.

Mask 15 Photographs, Respironics Inc., Paediatric Mask.

Mask 16 Photographs, Hans Rudolph Inc., Hans Rudolph Silicone Rubber Face Mask/8900.

* cited by examiner

MASK AND VENT ASSEMBLY THEREFOR

CROSS REFERENCE TO RELATED APPLICATIONS

This application is a continuation of U.S. application Ser. No. 09/021,541, filed Feb. 10, 1998, now U.S. Pat. No. 6,561,190, the specification and drawings of which are incorporated herein by reference.

FIELD OF THE INVENTION

The present invention relates to a mask and a vent assembly therefor.

The mask and vent assembly according to the invention have been developed primarily for the venting of washout gas in the application of continuous positive airway pressure (CPAP) treatment in conjunction with a system for supplying breathable as pressurised above atmospheric pressure to a human or animal. Such a system is used, for example, in the treatment of obstructive sleep apnea (OSA) and similar sleep disordered breathing conditions. However, the invention is also suitable for other purposes including, for example, the application of assisted ventilation or respiration.

The term "mask" is herein intended to include face masks, nose masks, mouth masks, nasal pillows, appendages in the vicinity of any of these devices and the like.

BACKGROUND OF THE INVENTION

Treatment of OSA by CPAP flow generator systems involves the continuous delivery of air (or other breathable gas) pressurised above atmospheric pressure to a patient's airways via a conduit and a mask.

For either the treatment of OSA or the application of assisted ventilation, the pressure of the gas delivered to a patient can be at a constant level, bi-level (ie. in synchronism with patient inspiration and expiration) or autosetting in level to match therapeutic need. Throughout this specification the reference to CPAP is intended to incorporate a reference to any one of, or combinations of, these forms of pressure delivery.

The masks used in CPAP treatment generally include a vent for washout of the gas to atmosphere. The vent is normally located in the mask or in the gas delivery conduit adjacent the mask. The washout of gas through the vent is essential for removal of exhaled gases from the breathing circuit to prevent carbon dioxide "re-breathing" or build-up, both of which represent a health risk co the mask wearer. Adequate gas washout is achieved by selecting a vent size and configuration that will allow a minimum safe as flow at the lowest operating CPAP pressure, which, typically can be as low as around 4 cm $H_2O$ for adults and 2 cm $H_2O$ in paediatric applications.

Prior art masks are generally comprised of a rigid plastic shell which covers the wearer's nose and/or mouth. A flexible or resilient rim (or cushion) is attached to the periphery of the shell which abuts and seals against the wearer's face to provide a gas-tight seal around the nose and/or mouth.

A prior art washout vent utilized one or more holes or slits in the rigid shell or in a rigid portion of the delivery conduit to allow the washout gas to vent to atmosphere. In some masks, the holes or slits were formed during the moulding process. In others, they were drilled or cut as a separate step after the shell or conduit had been moulded.

The flow of as out the holes or slits in the shell or conduit to atmosphere creates noise and turbulence at the hole or slit outlet as the delivered gas, and upon expiration, the patient-expired gas (including $CO_2$) exits. Bi-level and autosetting gas delivery regimes tend to generate more noise than a constant level gas delivery regime. This is thought to be due to the extra turbulence created by the gas accelerating and decelerating as it cycles between relatively low and relatively high pressures. The noise adversely affects patient and bed-partner comfort.

Another prior art vent included hollow rivets or plugs manufactured from stainless steel or other rigid materials attached to openings in the rigid shell. The outer edges of the rivers were rounded to help reduce noise. However, this approach was expensive, required an extra production step and did not prove effective in reducing noise.

Another approach to reduce noise involved the use of sintered filters at the gas outlet of the mask shell. However, the filters were prone to blocking especially in the presence of moisture. Accordingly, sintered filters were impractical for use in CPAP treatment as they were easily blocked by the moisture from the patient's respiratory system or humidifiers or during the necessary regular cleaning of the mask and associated componentry.

Foam filters wrapped around the air outlets in the shell were also attempted. However, they also suffered from the disadvantages of being prone to blocking, difficult to clean and requiring constant replacement.

Remote outlet tubes have been used to distance the noise source from the patient. However, these tubes are difficult to clean, are prone to entanglement by the patient and/or their bed partner and suffer the further disadvantage that a volume of exhausted gas is retained in the rube adjacent he mask.

It is an object of the present invention to substantially overcome or at least ameliorate the prior art disadvantages and, in particular, to reduce the noise generated by gas washout through a mask.

SUMMARY OF THE INVENTION

Accordingly, the invention, in a first aspect, discloses a mask for use with a system for supplying breathable gas pressurised above atmospheric pressure to a human or animal's airways, the mask includes a mask shell which is, in use, in fluid communication with a gas supply conduit, a gas washout vent assembly, wherein at least the region of the mask shell or conduit surrounding or adjacent the vent assembly is formed from a relatively flexible elastomeric material.

In an embodiment, the entire mask is formed from the elastomeric material.

In another embodiment, the mask shell and/or conduit is formed from a relatively rigid material and the region surrounding or adjacent the vent assembly is formed from the relatively flexible elastomeric material.

In a second aspect, the invention discloses a vent assembly for the washout of gas from a mask or conduit used with a system for supplying breathable gas pressurized above atmospheric pressure to a human or animal, wherein the vent assembly is formed from the relatively flexible elastomeric material.

In a preferred embodiment, the vent assembly is an insert of relatively flexible elastomeric material, wherein the insert is attachable to the mask shell or conduit. The insert preferably has at least one orifice therethrough.

In a preferred form, the rigid plastics mask shell is formed from polycarbonate and the insert is formed from Silastic™ or Santoprene™.

Desirably, the insert is substantially crescent-shaped and includes a plurality of orifices therethrough.

The insert preferably includes a groove around its periphery, the groove adapted to locate the insert against a correspondingly sized rim of an opening formed in the mask shell or conduit.

In other embodiments, the insert is substantially circular, triangular, cross or peanut shaped.

The mask shell and/or the conduit can desirably also include one or more inserts.

BRIEF DESCRIPTION OF THE DRAWINGS

Preferred embodiments of the invention will now be described, by way of examples only, with reference to the accompanying drawings in which.

DESCRIPTION OF THE PREFERRED EMBODIMENTS

Figure 1:
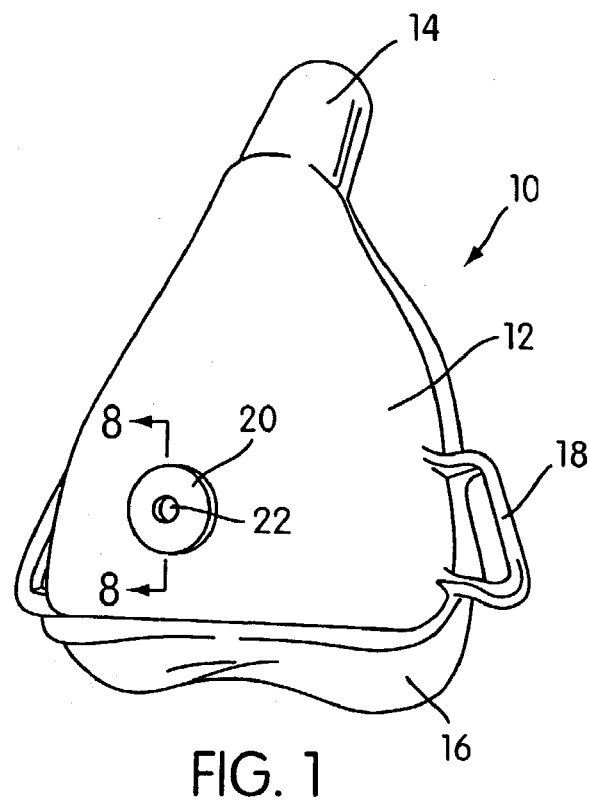
FIG. 1 is a perspective view of a first embodiment.
Figure 2:
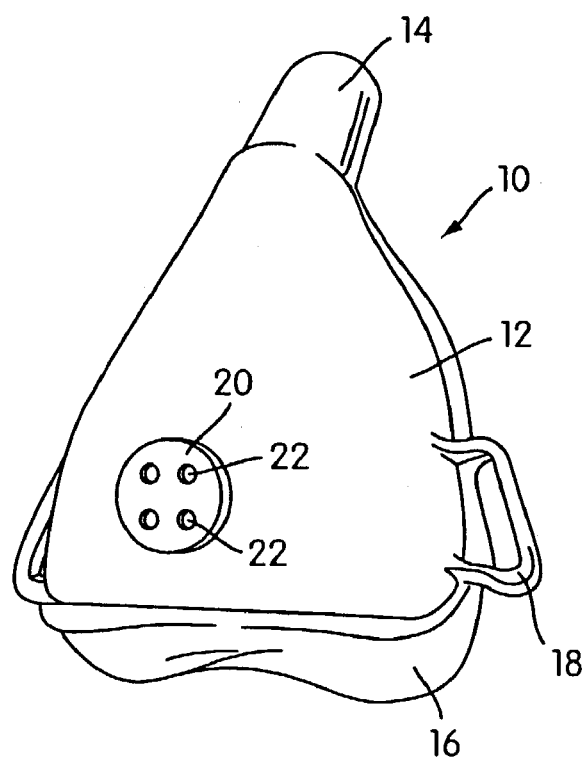
FIG. 2 is a perspective view of a second embodiment.

Referring firstly to FIG. 1, there is shown a mask 10 for use with a system (not shown) for supplying breathable gas pressurised above atmospheric pressure to a human or animal's airways. The mask includes a rigid plastics shell 12 having an inlet tube 14 for connection to a supply conduit to communicate breathable gas from a flow generator (not shown) to the nasal passages of the mask wearer. The mask shell 12 also includes a flexible sealing membrane 16 which is used to provide a gas tight seal between the face of the wearer and the interior of the shell 12. The shell 12 also includes lugs 18 for connecting the mask 10 to a head strap (not shown) to retain the mask in place.

Figure 8:
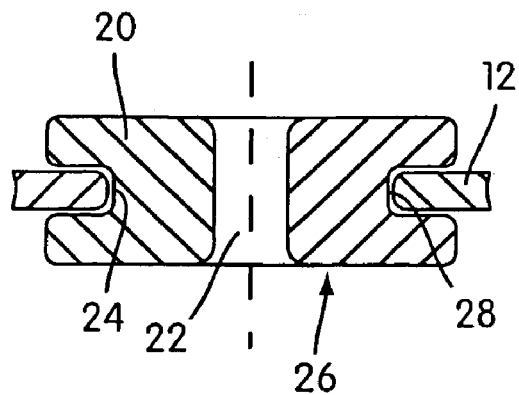
FIG. 8 is a partial cross-sectional view of the first embodiment along the line 8—8 of FIG. 1.

The mask includes a Silastic™ insert 20 through which is provided an orifice 22 for gas washout. As best shown in FIG. 8, the insert 20 has a recess or groove 24 around its periphery. A correspondingly sized opening 26 bounded by a rim 28 is provided in the shell 12 to enable the insert 20 to be retained in place in the fashion of a grommet. The opening 26 can be moulded in the shell 12 or drilled or punched as a post-moulding step. The flexibility of the Silastic™ allows the insert 20 to be initially squeezed through the opening 26 before resiliently expanding to the configuration shown in FIG. 8 and engaging the rim 28.

As seen in FIG. 8. orifice 22 has a cross-sectional contour from a face side of the orifice to an atmosphere side of the orifice. In FIG. 8, the contour is shown as being symmetrical between the face side of the orifice and the atmosphere side of the orifice with a central portion of the orifice contour being of constant diameter. After the insert 20 is positioned in opening 26 of mask shell 12, the contour remains substantially constant in size as gas is passed therethrough.

FIGS. 2 to 7 show further embodiments in which corresponding reference numerals are used to indicate like features. In all these embodiments the insert 20 has an external groove or recess 24 which engages the rim 28 of a corresponding shaped opening 26 in the mask shell 12 to retain the insert 20 in place.

In the embodiment shown in FIGS. 2 to 5 and 7 the insert 20 includes more than one orifice 22. In the embodiment shown in FIG. 6, two inserts 20 are provided in the shell 12.

Figure 9:
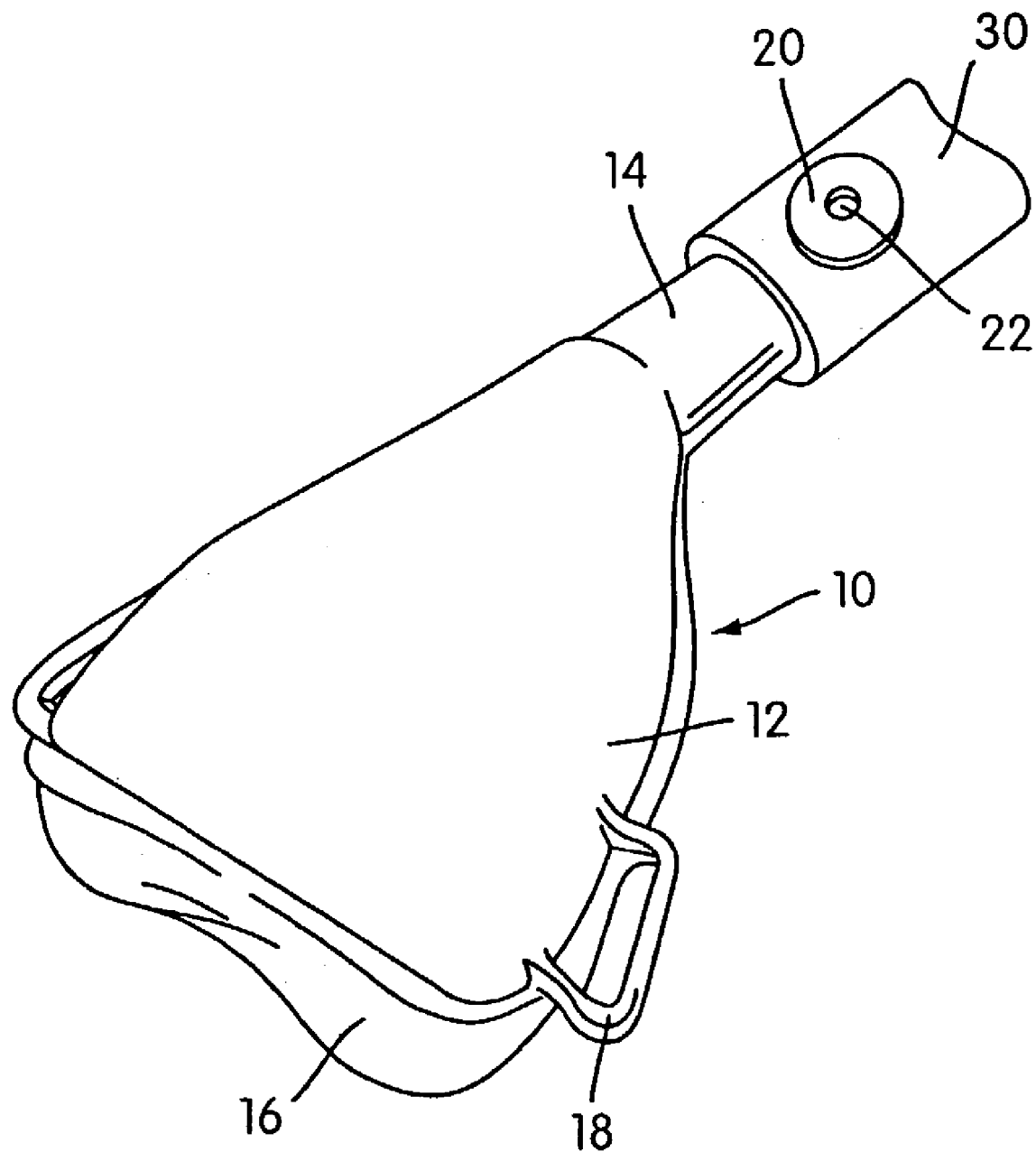
FIG. 9 is a perspective view of an eighth embodiment.

In the embodiment shown in FIG. 9, the insert 20 is provided in a as supply conduit 30.

Figure 3:
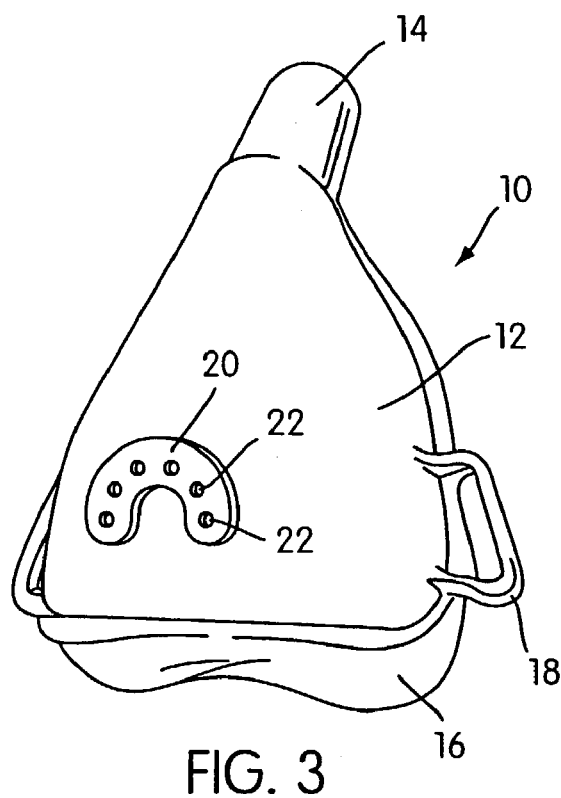
FIG. 3 is a perspective view of a third embodiment.
Figure 4:
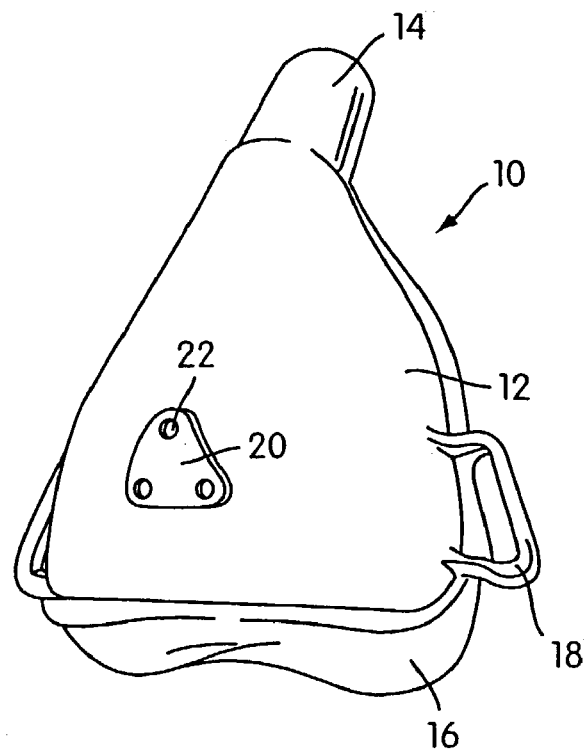
FIG. 4 is a perspective view of a fourth embodiment.
Figure 5:
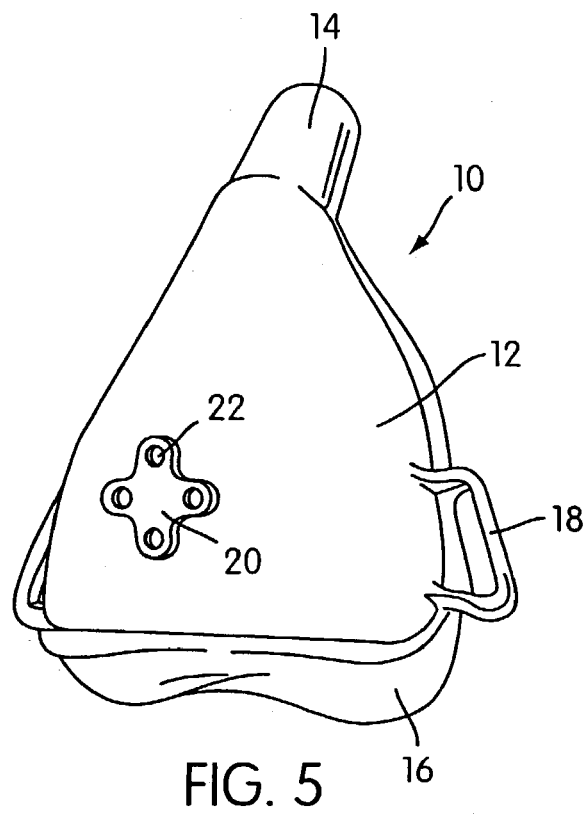
FIG. 5 is a perspective view of a fifth embodiment.
Figure 6:
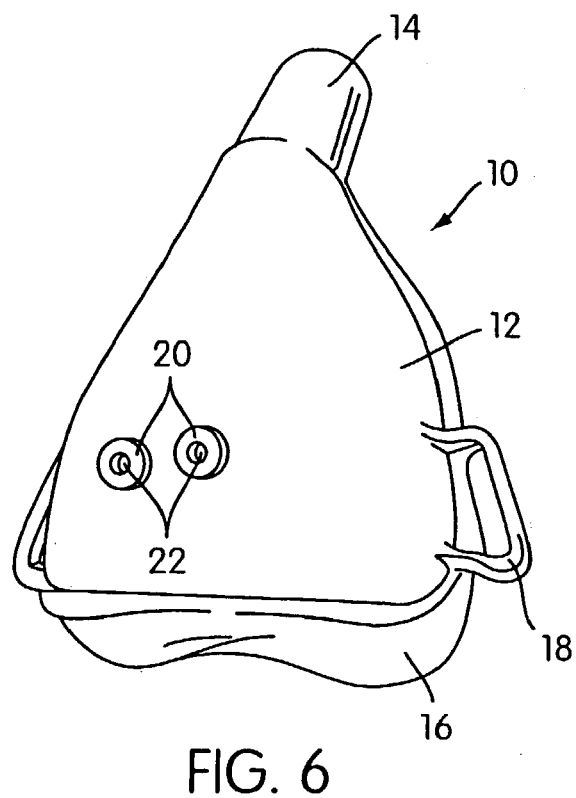
FIG. 6 is a perspective view of a sixth embodiment.
Figure 7:
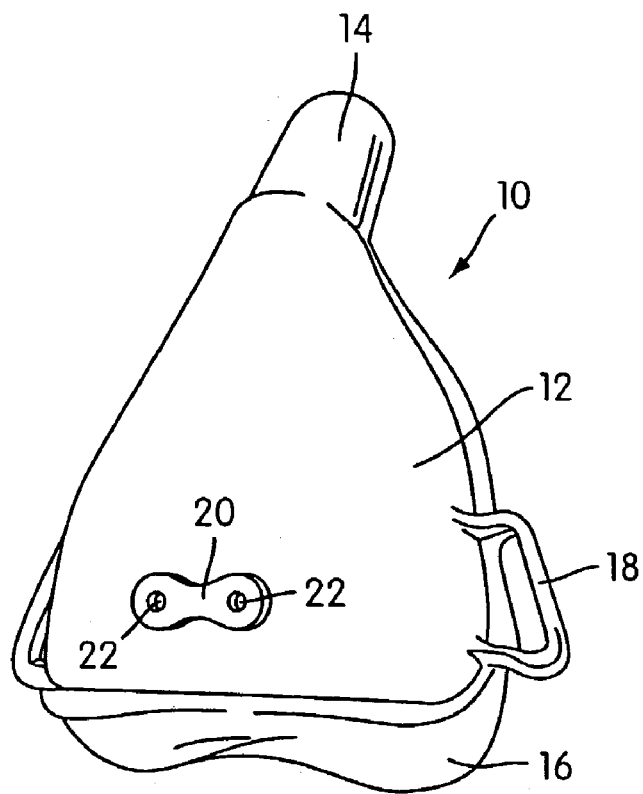
FIG. 7 is a perspective view of a seventh embodiment.
Figure 10:
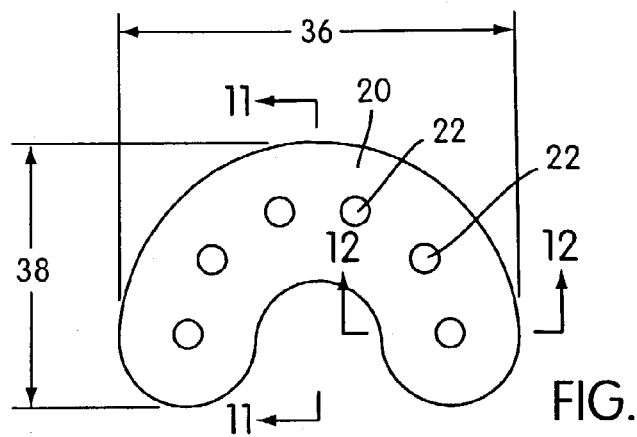
FIG. 10 is a plan view of the insert of the third embodiment.
Figure 11:
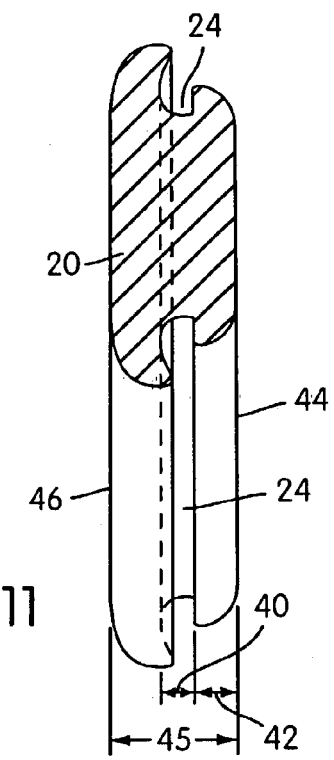
FIG. 11 is a cross-sectional view of the third embodiment insert along the line 11—11 of FIG. 10.
Figure 12:
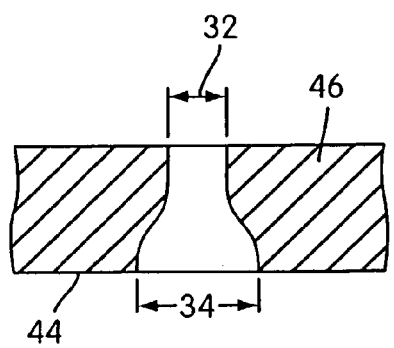
FIG. 12 is a partial cross-sectional view of the third embodiment insert along the line 12—12 of FIG. 10.

FIGS. 10 to 12 show the insert 20 of the third embodiment of FIG. 3. The dimensions 32, 34, 36, 38, 40, 42 and 45 are approximately diameter 1.73 mm, diameter 3.30 mm, 28.80 mm, 19.00 mm, 1.20 mm, 1.20 mm and 3.60 mm respectively.

The side 44 of the insert 20 faces the parient's face in use and the side 46 faces atmosphere.

The mask shell 12 is manufactured from polycarbonate. Other rigid plastics materials can equally be used. The insert 20 can be manufactured from an elastomer sold as Silastic™ (produced by the Dow Corning Corporation) or a thermoplastic elastomer sold as Santoprene™ (produced by Monsanto). Other flexible elastomeric materials can be used also.

The mask 10 produces less noise than an identical mask having a similar sized and shaped orifice(s) formed directly in the mask shell 12 instead of formed in the flexible insert 20. It is thought that the noise reduction occurs due to the flexible insert 20 damping vibrations caused by air passage through the orifice(s) 22 which produce vibrations or similar in the mask shell 12.

A prototype of the embodiment of the invention shown in FIG. 3 has been tested over a range of constant and bi-level CPAP treatment pressures. For comparison purposes, an identical mask to that shown in FIG. 3 but formed entirely from polycarbonate and having six identical arcuately spaced boles 22 drilled directly through the mask shell was also tested. In both masks the six holes had a diameter of 1.7 mm. The results of the test are summarised in the Tables below:

TABLE 1

Constant leval gas delivery

| Pressure | Noise levels 1 m from mask (dBA) | |
|---|---|---|
| (cm H$_2$O) | With flexible insert | Without flexible insert |
| 4 | 26.8 | 35.2 |
| 10 | 33.4 | 43.1 |
| 18 | 39.3 | 49.2 |

TABLE 2

Bi-level gas delivery

| Pressure | Noise levels 1 m from mask (dBA) | |
|---|---|---|
| (cm H$_2$O) | With flexible insert | Without flexible insert |
| 5–10 | 30.8–38.5 | 37.2–43.0 |
| 10–15 | 38.6–43.7 | 42.9–47.9 |

As the results show, the mask shown in FIG. 3 produced less radiated noise than a similar mask not including the flexible elastomeric insert 20 representing a significant advantage in terms of the comfort of the mask wearer and their bed partner.

In addition to the noise reduction discussed above, the masks 10 possesses other advantages over those of the prior art. Firstly, the insert 20 is very easy to install into the mask shell 12 during either assembly of the mask which, is often supplied in kit form, or before and after cleaning which is regularly required and often carried out in the home environment. Secondly, the mask shell 12 may be produced with a single size of opening 26 and provided with a range of different inserts 20 which allows the outlet size to be "tuned" to give an optimum gas washout rate for a particular patient's treatment pressure level.

Although the invention has been described with reference to specific examples, it will be appreciated by those skilled in the art, that the invention may be embodied in many other forms.

We claim:

1. A CPAP mask assembly for use with a system for supplying breathable gas pressurized above atmospheric pressure to a human or animal, the CPAP mask assembly comprising:
   a mask adapted to be in fluid communication with a gas supply conduit; and
   a vent assembly provided to the mask, the vent assembly including at least one gas washout orifice extending from an inner side of the vent assembly placed, in use, adjacent the human or animal's face to an outer side placed, in use, adjacent the atmosphere, the gas washout orifice being open in use, wherein
   a cross-sectional area of the orifice at the inner side of the vent assembly is larger than a cross-sectional area of the orifice at the outer side of the vent assembly,
   the inner side of the vent assembly extends inside the mask and the outer side of the vent assembly extends outside the mask, and
   the orifice does not substantially change shape upon application of pressurized gas at a level suitable for CPAP treatment for obstructive sleep apnea.

2. A CPAP mask assembly as claimed in claim 1, wherein the orifice includes a first substantially cylindrical portion adjacent the inner side of the vent assembly, a second substantially cylindrical portion adjacent the outer side of the vent assembly and a tapering portion between the first substantially cylindrical portion and the second substantially cylindrical portion.

3. A CPAP mask assembly as claimed in claim 2, wherein the second substantially cylindrical portion and the tapering portion are of approximately equal thickness in the axial direction of the orifice and are thicker than the first substantially cylindrical portion.

4. A CPAP mask assembly as claimed in claim 1, wherein the vent assembly is an insert of relatively elastomeric material and is selectively attachable to and detachable from the mask.

5. A CPAP mask assembly as claimed in claim 4, wherein the insert is fonned from one of SILASTIC™ and SANTOPRENE™.

6. A CPAP mask assembly as claimed in claim 4, wherein the insert includes a groove around its periphery, the groove locating the insert against a correspondingly sized rim of an opening formed in the mask.

7. A CPAP mask assembly as claimed in claim 4, wherein the insert is substantially crescent shaped.

8. A CPAP mask assembly as claimed in claim 1, wherein first and second ends of the orifice are located proximate an opening of the mask at, respectively, the inner side of the vent assembly and the outer side of the vent assembly.

9. A CPAP mask assembly as claimed in claim 1, wherein a thickness of the vent assembly is greater than an inner diameter of the orifice.

10. A CPAP mask assembly as claimed in claim 1, wherein the orifice does not substantially change shape upon application of pressurized gas less than about 18 cmH$_2$O.

11. A CPAP mask assembly as claimed in claim 1, wherein the orifice does not substantially change shape upon application of pressurized gas in the range of 4–18 cmH$_2$O.

12. A CPAP mask assembly as claimed in claim 1, wherein the orifice does not substantially change shape upon application of pressurized gas in the range of 5–15 cmH$_2$O.

13. A CPAP assembly as claimed in claim 1, wherein the orifice has a length of about 3.60 mm, an inner diameter at the inner side of about 3.30 mm, and an outer diameter at the outer side of about 1.73 mm.

14. A CPAP mask assembly as claimed in claim 1, wherein the vent assembly includes an insert formed from one of SILASTIC™ and SANTOPRENE™ and the orifice has a length of about 3.60 mm, an inner diameter at the inner side of about 3.30 mm, and an outer diameter at the outer side of about 1.73 mm, and wherein the orifice does not substantially change shape upon application of pressurized gas less than about 18 cmH$_2$O.

15. A CPAP mask assembly as claimed in claim 1, wherein a ratio of an inner diameter at the inner side of the orifice to an outer diameter at the outer side of the orifice is about 2.

16. A CPAP mask assembly as claimed in claim 1, wherein the orifice includes a central portion having a curved portion that transitions a larger cross-sectional area of the orifice at the inner side to a smaller cross-sectional area of the orifice at the outer side.

17. A CPAP mask assembly for use with a system for supplying breathable gas pressurized above atmospheric pressure to a human or animal for treatment of obstructive sleep apnea, the CPAP mask assembly comprising:
   a mask adapted to be in fluid communication with a gas supply conduit; and
   a vent assembly provided to the mask, the vent assembly including at least one gas washout orifice extending from an inner side of the vent assembly placed, in use, adjacent the human or animal's face to an outer side placed, in use, adjacent the atmosphere, the gas washout orifice being open in use, and a cross-sectional area of the orifice at the inner side of the vent assembly is larger than a cross-sectional area of the orifice at the outer side of the vent assembly; wherein
   the orifice includes a first substantially cylindrical portion adjacent the inner side of the vent assembly, a second substantially cylindrical portion adjacent the outer side of the vent assembly and a tapering portion between the first substantially cylindrical portion and the second substantially cylindrical portion, and
   the orifice does not substantially change shape upon application of pressurized gas at a level suitable for CPAP treatment for obstructive sleep apnea.

18. A CPAP mask assembly as claimed in claim 17, wherein the tapering portion is present independent of whether the mask is in use.

19. A mask assembly for use wit a system for supplying breathable gas pressurized above atmospheric pressure to a human or animal's airways, the mask assembly comprising:

a mask including an inlet tube that is, in use, adapted to be in fluid communication with a gas supply conduit pressurized above atmospheric pressure; and a gas washout vent assembly located on the mask, wherein the gas washout vent assembly comprises an elastic, deformable insert that can be removably inserted into an opening provided on the mask, the insert includes a first surface to engage an inner surface of the mask, a second surface to engage an outer surface of the mask and a groove between the first and second surfaces to receive an edge defining the opening of the mask;

the insert includes at least one gas washout orifice with an outlet opening positioned, in use, adjacent atmosphere, the orifice does not substantially change shape upon application of pressurized gas at a level suitable for CPAP treatment of obstructive sleep apnea, a cross-sectional area of orifice oriented towards an inner side of the insert is larger than a cross-sectional area of the orifice oriented towards the outlet opening of the insert, and a thickness of the insert is greater than a diameter of orifice.

20. A mask assembly as claimed in claim 19, wherein at least one orifice includes at least two orifices.

21. A mask assembly as claimed in claim 19, wherein, in use, pressure delivered to the patient is above atmospheric pressure at least during the inhalation and exhalation phases of the patient's breathing cycle, during which phases gas washout through the orifice is possible.

22. An assembly for use with a system for supplying breathable gas pressurized above atmospheric pressure to a patient's airways, the assembly comprising:

a patient interface including an air inlet tube that is, in use, adapted to be in fluid communication with a gas supply conduit pressurized above atmospheric pressure at least during inhalation and exhalation phases of the patient's breathing cycle, the patient interface including a sealing membrane to provide a gas tight seal with the patient in use;

a gas washout vent assembly including at least two gas washout orifices extending towards an outer side of the patient interface positioned, in use, adjacent the atmosphere, each said orifice being open in use and having a cross-sectional area at an inner side that is larger than a cross-sectional area at the outer side, wherein the outer side of each said orifice is substantially circular, each said orifice includes a central portion connecting the inner and outer sides, the central portion having a cross-sectional area that varies along a length of the central portion, the patient interface is defined at least in part by a wall structure wade of a relatively rigid material compared to the vent assembly, and the vent assembly is made of an elastomeric material, the vent assembly comprises an insert that can be removably inserted into an opening on the mask, the insert including a first surface to engage an inner surface of the mask, a second surface to engage an outer surface of the mask, and a groove provided between the first and second surfaces to receive a rim of the opening, the orifice does not substantially change shape upon application of pressurized gas, and the inner side of each said orifice is located proximate the opening of the mask.

23. A mask assembly for use with a system for supplying breathable gas pressurized above atmospheric pressure to a human or animal patient's airways, the mask assembly comprising:

a mask including an inlet tube which is adapted for fluid connection with a gas supply conduit, a region of the mask defining a vent opening adapted for gas washout, and an insert formed of an elastomeric material positioned within said vent opening, said insert having at least two orifices provided for gas washout, said each orifice having a cross-sectional contour structured and configured to remain substantially constant in size as gas is passed therethrough, wherein the mask is formed from a material that is relatively rigid compared to the elastomeric material of the insert, the insert comprises a groove around a periphery of the insert, the groove being adapted to locate the insert against a correspondingly sized rim of the vent opening after being resiliently squeezed through the vent opening during assembly, the insert groove is substantially circular, and a portion of the cross-sectional contour of each said orifice near an atmosphere side of the respective orifice is smaller than a portion of the cross-sectional contour of each said orifice near a side of the orifice oriented towards the patient's side of the mask.

24. A CPAP mask assembly for use with a system for supplying breathable gas pressurized above atmospheric pressure to a human or animal patient, the CPAP mask assembly comprising:

a mask adapted to be in fluid communication with a gas supply conduit: and a vent assembly provided to the mask, the vent assembly including an insert formed from an elastomeric material, said insert having at least two orifices therethrough for gas washout, each said orifice having a cross-sectional contour structured and configured to remain substantially constant in size as gas is passed therethrough at a pressure level suitable for CPAP treatment for obstructive sleep apnea, wherein the insert includes a groove around a periphery of the insert, the groove abutting against a correspondingly sized rim of the mask vent opening, the insert groove is substantially circular, and a portion of the cross-sectional contour of each said orifice near an atmosphere side of the orifice is smaller than a portion of the cross-sectional contour of the orifice near a side of the orifice oriented towards the patient's side of the mask.

25. A mask assembly for use with a system for supplying breathable gas pressurized above atmospheric pressure to a human patient's airways, the mask assembly including:

a mask including an inlet tube which is adapted for fluid communication with a gas supply conduit, said mask including an opening therein; and an insert fanned of an elastomeric material at least partially positioned within said opening, said insert having at least two orifices provided for gas washout at least when the patient is in the inspiratory phase of the breathing cycle, wherein said mask adjacent said opening has a first thickness and said insert has a second thickness that is greater than said first thickness, the mask is formed from a relatively rigid material compared to the elastomeric material of the insert, the insert is selectively attachable to and detachable from the mask, and the insert comprises a groove around a periphery of the insert, the groove being adapted to locate the insert against a correspondingly sized rim of the mask opening, the insert being structured to resiliently expand to engage the rim during assembly.

26. The mask assembly as claimed in claim 25, wherein the insert groove is substantially circular, and a portion of each said orifice near an atmosphere side of the mask is smaller than a portion of the orifice oriented towards a side of the mask on the patient's side.

27. The mask assembly as claimed in claim 25, wherein the mask includes a shell that includes the first thickness, and the second thickness is measured along a similar axis as the first thickness.

28. A mask assembly for use with a system for supplying breathable gas pressurized above atmospheric pressure to a human patient's airways, the mask assembly including:

a mask including an inlet tube and an interior chamber which is adapted for fluid communication with a gas supply conduit via the inlet tube, said mask including an opening in communication with atmosphere and having a thickness in a direction substantially normal to a surface of said mask adjacent said opening; and an insert of an elastomeric material, the insert at least partially positioned within said opening and having at least one orifice provided for gas washout, wherein the orifice does not substantially change shape upon application of pressurized gas at a level suitable for CPAP treatment for obstructive sleep apnea, the mask is formed from a material that is relatively rigid compared to the elastomeric material of the insert, the insert is attachable to the mask via compression and resilient expansion, the insert comprises a groove around a periphery of the insert, the groove being adapted to locate the insert against a correspondingly sized rim of the mask opening, the insert groove is substantially circular, and a portion of the orifice near an atmosphere side of the mask is smaller than a portion of the orifice oriented towards a side of the mask on the patient's side.

29. A mask assembly as claimed in claim 28, wherein the at least one orifice includes at least two orifices.

30. A mask assembly for use with a system for supplying breathable gas pressurized above atmospheric pressure to a patient's airways, the mask assembly comprising:

a mask having an inlet tube adapted for fluid connection with a gas supply conduit;

a vent opening for gas washout formed in the mask; and an insert formed of an elastomeric material positioned within the vent opening, said insert having at least two orifices provided for gas washout, each said orifice having a cross-sectional contour structured and configured to remain substantially constant in size as gas is passed therethrough, wherein:

the mask is fonned from a material that is relatively rigid compared to the elastomeric material of the insert, the insert includes a groove around a periphery of the insert, the groove being adapted to locate the insert against a correspondingly sized rim of the vent opening via resilient expansion of the insert, a size of a first end of each said orifice oriented towards the patient side in use is larger than a size of a second end of each respective orifice oriented towards an atmospheric side in use, a portion of each orifice between the first and second ends varying in size along a length thereof, and the mask has a first thickness adjacent the vent opening that is less than a second thickness of the insert.

31. The mask assembly as claimed in claim 30, wherein the mask includes a shell that is formed from a material that is relatively rigid compared to the elastomeric material of the insert.

32. A CPAP mask assembly for use with a system for supplying breathable gas pressurized above atmospheric pressure to a human or animal, the CPAP mask assembly comprising:

a mask adapted to be in fluid communication with a gas supply conduit; and a vent assembly including at least one gas washout orifice, in use, communicating between atmosphere and a first pressure region, higher than atmospheric pressure, the gas washout orifice being open in use, wherein a cross-sectional area of the orifice towards the first pressure region is larger than a cross-sectional area of the orifice oriented towards atmosphere, an inner side of the vent assembly is structured to extend inside the mask or conduit and an outer side of the vent assembly is structured to extend outside the mask or conduit, the orifice does not substantially change shape upon application of pressurized gas at a level suitable for CPAP treatment for obstructive sleep apnea, wherein the vent assembly includes a plurality of said orifices, and wherein the vent assembly is an insert of relatively elastomeric material and is selectively attachable to and detachable from one of the mask and conduit.

33. A CPAP mask assembly including the vent assembly as claimed in claim 32, wherein the mask includes a shell.

34. A CPAP mask assembly as claimed in claim 33, wherein the insert is provided to the shell.

35. A CPAP mask assembly as claimed in claim 33, wherein the insert is provided upstream of the shell, wherein upstream is measured in terms of the flow direction of said breathable gas towards the patient.

36. A CPAP mask assembly as claimed in claim 35, wherein the insert is provided on the conduit.

37. A CPAP mask assembly for use with a system for supplying breathable gas pressurized above atmospheric pressure to a human or animal for treatment of obstructive sleep apnea, the CPAP mask assembly comprising:

a mask adapted to be in fluid communication with a gas supply conduit; and an insert provided to the mask, the insert including at least one gas washout orifice extending therethrough, the insert being dimensioned and constricted of a silicone material such that the at least one orifice does not substantially change shape upon application of pressurized gas, wherein the insert is formed from one of SILASTIC™ and SANTOPRENE™ and the orifice has a length of about 3.60 mm, an inner diameter at the inner side of about 3.30 mm, and an outer diameter at the outer side of about 1.73 mm, and wherein the orifice does not substantially change shape upon application of pressurized gas less than about 18 cmH$_2$O.

38. A CPAP mask assembly for use with a system for supplying breathable gas pressurized above atmospheric pressure to a human or animal for treatment of obstructive sleep apnea, the CPAP mask assembly comprising:

a mask adapted to be in fluid communication with a gas supply conduit; and an insert provided to the mask, the insert including at least one gas washout orifice extending therethrough, the insert being dimensioned and constructed of a silicone material effective for maintaining the shape or cross-sectional contour of the at least one orifice upon application of pressurized gas, wherein the insert is formed from one of SILASTIC™ and SANTOPRENE™ the insert has a thickness of about 3.60 mm, an inner diameter at the inner side is larger than an outer diameter at the outer side, and wherein the orifice does not substantially change shape upon application of pressurized gas less than 18 cmH₂O.

39. A mask assembly for use with a system for supplying breathable gas pressurized above atmospheric pressure to a patient's airways, the mask assembly comprising:

a mask having an inlet tube adapted for fluid communication with a gas supply conduit;

a substantially circular vent opening formed in the mask and a substantially circular rim surrounding the vent opening; and a gas washout vent assembly positioned in covering relation with respect to the vent opening, the gas washout vent assembly including an insert formed of an elastomeric material, the insert including a plurality of gas washout orifices each having a cross-sectional area on a first side of the insert that is larger than a cross-sectional area on a second side of the insert, and each orifice including a central portion connecting the first and second sides having a cross-sectional area that varies along at least a portion of a length of the central portion, the insert being removably insertable into the vent opening, the insert including a first surface adapted to engage an inner surface of the mask, a second surface adapted to engage an outer surface of the mask, and a substantially circular groove provided between the first and second surfaces to receive the substantially circular rim of the vent opening.

40. The mask assembly as claimed in claim 39, wherein the cross-sectional area of the central portion tapers along substantially an entire length of the central portion.

41. A mask assembly for use with a system for supplying breathable gas pressurized above atmospheric pressure to a patient's airways, the mask assembly comprising:

a mask having an inlet tube adapted for fluid connection with a gas supply conduit;

a vent opening for gas washout formed in the mask; and an insert formed of an elastomeric material positioned within the vent opening, said insert having a gas washout orifice having a cross-sectional area on a first side of the insert that is larger than a cross-sectional area on a second side of the insert, and said orifice including a central portion between the first and second sides having a cross-sectional area that varies along at least a portion of a length of the central portion, wherein:

the orifice is open in use at least during the inhalation and exhalation phases of the patient's breathing cycle, the mask is defined at least in part by a wall structure made of relatively rigid material compared to the elastomeric material of the insert, the wall structure defining a rim surrounding the vent opening, and the insert is removably insertable into the vent opening, the insert including a first surface adapted to engage an inner surface of the mask, a second surface adapted to engage an outer surface of the mask, and a groove provided between the first and second surfaces to receive the rim via resilient expansion of the insert.

42. A mask assembly as claimed in claim 41, wherein the mask includes a nose mask.

43. A mask assembly as claimed in claim 41, wherein an inner side of the insert extends inside the mask and an outer side of the insert extends outside the mask.

44. A CPAP mask assembly for use with a system for supplying breathable gas pressurized above atmospheric pressure to a user for treatment of obstructive sleep apnea, the CPAP mask assembly comprising:

a mask having an inlet tube that is, in use, adapted to be in fluid communication with a gas supply conduit, said mask including a shell made from polycarbonate or another rigid plastic material, the shell being provided with a sealing membrane to provide a gas tight seal with the user in use; and a vent provided to the shell, the vent including at least four gas washout orifices, each said orifice having an inner side that, in use, is positioned adjacent the user's face, and an outer side that, in use, is positioned adjacent atmosphere, each said orifice being open in use at least during the inhalation and exhalation phases of the user's breathing cycle, wherein each said orifice has a substantially round cross section along its length, a cross-sectional size or area of each orifice at the inner side is larger than a cross-sectional size or area of the orifice at the outer side, and a transition portion between the inner and outer sides of each said orifice has a cross-sectional size or area that varies along at least a portion of a length thereof, an inner end of each said orifice extends inside the shell, and a length of each orifice is greater than a thickness of a portion of said shell surrounding the orifice.

45. A CPAP mask assembly as claimed in claim 44, wherein the vent includes six orifices.

46. A CPAP mask assembly as claimed in claim 45, wherein a ratio of an inner diameter at the inner side of the orifice to an outer diameter at the outer side of the orifice is about 1.9.

47. A CPAP mask assembly as claimed in claim 45, wherein the length of each said orifice is greater than an inner diameter at the inner side of each said orifice.

48. A CPAP mask assembly as claimed in claim 45, wherein said orifices are separated from each other by at least a diameter of the orifice at the outer side.

49. A CPAP mask assembly as claimed in claim 45, wherein an axis defined within the orifice extends substantially linearly from the inner aide to the outer side.

50. A CPAP mask assembly as claimed in claim 45, wherein the shell includes a lug on each side thereof for connecting the mask to a headgear strap to retain the mask in place relative to the user in use.

51. A CPAP mask assembly as claimed in claim 45, wherein the length of each orifice is about 3 times a thickness of the shell.

52. A CPAP mask assembly as claimed in claim 45, wherein the length of each said orifice is about 3.60 mm, and each said orifice has an inner diameter at the inner side of about 3.30 mm, and an outer diameter at the outer side of about 1.73 mm.

53. A CPAP mask assembly as claimed in claim 45, wherein the vent includes an elastomeric insert and the orifices are provided in the insert.

* * * * *